(12) United States Patent
Duyvesteyn

(10) Patent No.: US 7,824,453 B2
(45) Date of Patent: Nov. 2, 2010

(54) BIODIESEL PRODUCTION AND USE IN OIL SANDS PROCESSING

(75) Inventor: Willem P. C. Duyvesteyn, Reno, NV (US)

(73) Assignee: Marathon Oil Canada Corporation, Calgary, Alberta (CA)

( * ) Notice: Subject to any disclaimer, the term of this patent is extended or adjusted under 35 U.S.C. 154(b) by 1083 days.

(21) Appl. No.: 11/517,730

(22) Filed: Sep. 8, 2006

(65) Prior Publication Data

US 2008/0060257 A1    Mar. 13, 2008

(51) Int. Cl.
    *C10L 1/18* (2006.01)
(52) U.S. Cl. .......................... 44/308; 208/390; 208/391
(58) Field of Classification Search .................. 44/308; 208/390, 391
    See application file for complete search history.

(56) References Cited

U.S. PATENT DOCUMENTS

| | | | |
|---|---|---|---|
| 4,046,668 | A | 9/1977 | Farcasiu et al. |
| 4,224,138 | A | 9/1980 | Kruyer |
| 4,347,118 | A | 8/1982 | Funk et al. |
| 4,846,964 | A | 7/1989 | Scott et al. |
| 5,084,160 | A | 1/1992 | Stewart et al. |
| 5,143,598 | A | 9/1992 | Graham et al. |
| 5,295,665 | A | 3/1994 | Mackie |
| 5,670,345 | A | 9/1997 | Srivastava et al. |
| 5,872,289 | A | 2/1999 | Appleby et al. |
| 6,764,542 | B1 * | 7/2004 | Lackey et al. ............... 106/277 |
| 6,768,015 | B1 | 7/2004 | Luxem et al. |
| 6,822,105 | B1 | 11/2004 | Luxem et al. |
| 6,827,841 | B2 | 12/2004 | Kiser et al. |
| 6,965,044 | B1 | 11/2005 | Hammond et al. |
| 7,588,682 | B2 * | 9/2009 | Norman ...................... 208/391 |
| 2005/0211434 | A1 | 9/2005 | Gates et al. |
| 2006/0076274 | A1 | 4/2006 | Duyvesteyn et al. |

OTHER PUBLICATIONS

Campbell, J., National Biodiesel Board 2005 Annual Meeting, Marina Marriott, Ft. Lauderdale, FL (Feb. 1, 2005).
Cohen, et al., "Degradation of Coal by Fungi Polyporus Versicolor and Poria Monticola," Appl. Environ. Microbiol. 44 (1):23-27 (Jul. 1982).
Gallmetzer, et al., "Efflux of Organic Acids in *Penicillium simplicissimum* is an Energy-Spilling Process, Adjusting the Catabolic Carbon Flow to the Nutrient Supply and the Activity of Catabolic Pathways," Microbiology 148:1143-1149 (2002).

(Continued)

*Primary Examiner*—Cephia D Toomer
(74) *Attorney, Agent, or Firm*—Holland & Hart LLP

(57) ABSTRACT

A method for obtaining heavy oil is disclosed. The method includes mixing a material including heavy oil (e.g., oil sand) with a solvent including biodiesel to form a mixture and separating the mixture into a oil-enriched solvent phase and a residual sand phase. The method also can include introducing a solvent including biodiesel into an in-situ geological formation including heavy oil and collecting a mixture including biodiesel and heavy oil from the formation. For example, the mixture can be collected after the solvent travels through at least a portion of the formation by gravity. A method for producing biodiesel also is disclosed. The method includes microbially digesting asphaltenes to form a liquor including a fatty acid and reacting the fatty acid with an alcohol to produce biodiesel. This method can be used to convert petroleum asphaltenes and/or coal asphaltenes into biodiesel.

6 Claims, 4 Drawing Sheets

OTHER PUBLICATIONS

Rogoff, et al., "The Microbiology of Coal I. Bacterial Oxidation of Phenanthrene," Bureau of Mines, U.S. Dept. of the Interior, Region V, Bruceton, PA, 73:264-268 (Aug. 23, 1956).

Vicente, et al., "A Comparative Study of Vegetable Oils for Biodiesel Production in Spain," Energy & Fuels 20:394-398 (2006) (published on Web Nov. 8, 2005).

"Biodiesel Processing," 3 pp. (Mar. 22, 2004).

"Biodiesel Processing," biodiesel Handout for 2005 New Hampshire Science Teacher's Association Workshop UNH Biodiesel Group, http://www.unh.edu/p2/biodiesel, 27 pp. (2005).

"Soygold Environmental Solutions to Your Market Challenges," http://www.soygold.com/applications.htm, printed Mar. 6, 2007, 2 pp. (2007).

* cited by examiner

Coal and Penicillium Waxmanii

Coal "Bioleaching": from 2 to 8 Days

BIODIESEL PRODUCTION AND USE IN OIL SANDS PROCESSING

FIELD

This disclosure relates generally to the production of biodiesel by microbial processes and to the recovery of heavy oil from oil sands by solvent extraction using biodiesel.

BACKGROUND

The term "biodiesel" refers to methyl or ethyl esters that are generally between 8 and 25 carbons in length. Biodiesel typically is derived from tri-glyceride oils. Current sources of tri-glyceride oils for the production of biodiesel include plants (e.g., soybean, canola, corn, and sunflower), recycled cooking oil, and animal fat. Tri-glyceride oils can be converted into biodiesel by transesterification, which is a reaction to replace glycerol groups with alcohol groups. Catalysts useful for this reaction include sodium hydroxide and potassium hydroxide. Useful alcohol reactants include methanol and ethanol.

A variety of potential uses for biodiesel exist in addition to its most prominent use as fuel oil. The uses include various cleaning and solvent uses, such as hand cleaning, petroleum degreasing, paint removal, lubrication of metal cutting tools, adhesive removal, and rust prevention. In addition, U.S. Pat. No. 6,764,542 discloses the use of biodiesel as an additive for reducing the viscosity of asphalt. Similarly, U.S. Pat. No. 6,827,841 discloses the addition of biodiesel to petroleum pitch. Despite these disclosures, the widespread use of biodiesel for applications other than fuel applications has been limited.

SUMMARY

Disclosed herein are embodiments of a method for obtaining hydrocarbons and mixtures of hydrocarbons, such as heavy oil. In comparison to conventional methods, certain embodiments of the disclosed method can be more environmentally benign, safer and/or more efficient.

Some embodiments include mixing a material including heavy oil (e.g., oil sand or a petroleum-containing substrate) with a solvent including biodiesel to form a mixture and separating the mixture into a hydrocarbon-enriched solvent phase and a residual sand phase. The solvent includes, for example, between about 5% and about 100% biodiesel. The biodiesel can, for example, be derived from natural fats that have not been subjected to bleaching and/or deodorizing. After the separation, the residual sand phase can be transported underground to a location from which the material including heavy oil was withdrawn.

Some embodiments include combining a solid, asphaltene-containing material with a quantity of solvent sufficient to convert at least a portion of the solid, asphaltene-containing material into a liquid. Examples of solid, asphaltene-containing material include precipitates from alkane solvent processing of bitumen and pitch from elevated-temperature processing of heavy oil. The resulting liquid can be used as fuel to produce electric power or steam. Alternatively the liquid product can be further converted into an organic chemical product, such as a surfactant, an olefin, an alcohol, an ester or a combination thereof.

Some disclosed embodiments can include underground heavy oil recovery. These embodiments may include, for example, introducing a solvent including biodiesel (e.g., between about 5% and about 100% biodiesel) into an in-situ geological formation including heavy oil and collecting a mixture including biodiesel and heavy oil from the formation, such as after the solvent travels through at least a portion of the formation by gravity. The solvent can be introduced at a location at a higher elevation than the location at which the mixture is collected. After the mixture is collected, it can be transported above ground through a pipeline. A gas phase and/or water can be separated from the mixture before the heavy oil and biodiesel product is used or sold. At least a portion of the biodiesel in the mixture can be recovered and recycled.

Also disclosed are embodiments of a method for producing an ester (e.g., biodiesel) and embodiments of an ester (e.g., biodiesel) resulting from the method. The method includes, for example, microbially digesting a hydrocarbon phase (e.g., a hydrocarbon phase derived from biomass) to form a liquor including a fatty acid and reacting the fatty acid with an alcohol to produce an ester (e.g., biodiesel). The microbial digestion can occur by combining the hydrocarbon phase with a fungi culture, such as a culture of *penicillium waxmanii*. This method represents a particularly efficient way to derive usable fuel from abundant hydrocarbon resources, such as coal. For example, the hydrocarbon phase can include petroleum asphaltenes and/or coal asphaltenes, which are difficult to utilize in other processes. An example of an embodiment for converting coal into biodiesel includes combining coal with a fungi culture in a bioreactor, extracting a bioliquor from the bioreactor, settling spent coal residue from the bioliquor, and reacting the bioliquor with an alcohol to produce biodiesel. Any unreacted portion of the bioliquor can then be recycled back into the bioreactor for further processing.

It should be understood that this summary is not exhaustive, and that all embodiments do not necessarily include all features or advantages noted above. Furthermore, there are additional features, aspects, and advantages of various embodiments. They will become apparent as this specification proceeds.

DETAILED DESCRIPTION

Figure 1:
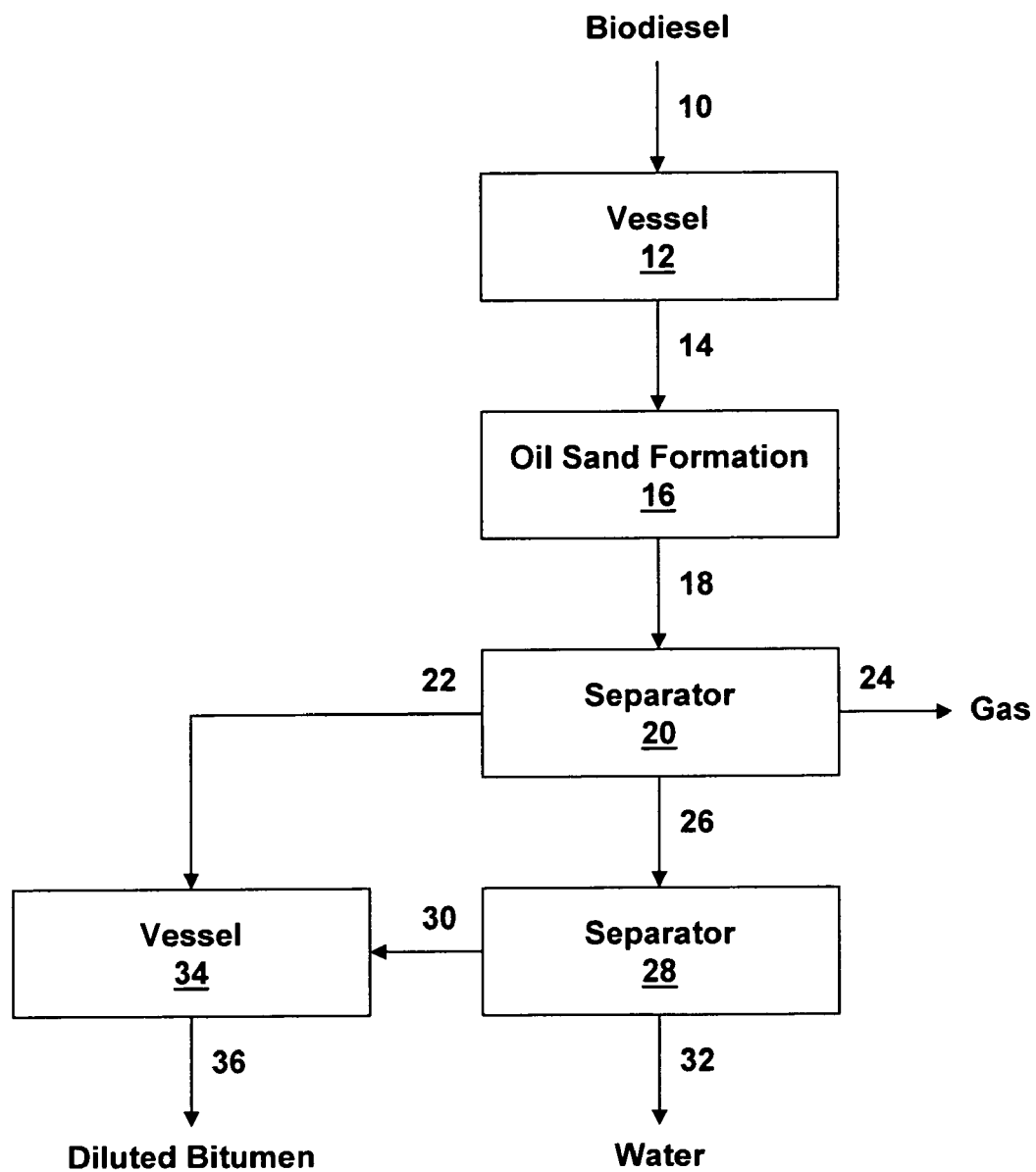
FIG. 1 is a schematic diagram representing embodiments of a process and apparatus for extracting heavy oil from oil sand using a biodiesel solvent.

Disclosed herein are various embodiments of a method for using biodiesel to extract heavy oil from materials that include heavy oil (e.g., oil sands), embodiments of a method for using biodiesel for in-situ heavy oil recovery, embodiments of a method for making biodiesel, and embodiments of a resulting biodiesel product.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. The term "includes" means "comprises." The method steps described herein, such as the separations, can be partial, substantial or complete unless indicated otherwise.

As used herein, the term "heavy oil" refers to hydrocarbons having an API gravity less than about 22°, such as bitumen. The phrase "oil sands" includes a variety of compositions that include both heavy oil and mineral components. Oil sands typically include sand, clay, heavy oil, and water. The heavy oil in oil sands typically includes resins and asphaltenes. Depending on the composition, oil sands can have varying levels of hardness. Some oil sands, such as oil shale, are in the form of a rocklike ore. Other oil sands are generally granular. Upon separation from the mineral components, heavy oil has many useful applications and can be refined into valuable commodities.

Extracting Heavy Oil with Biodiesel

Extracting usable oil from oil sand typically begins by separating heavy oil from mineral components of the oil sand. One example of a conventional method for performing this separation is described in U.S. Pat. No. 4,046,668 (the '668 patent). The '668 patent discloses heavy oil extraction with a mixture of light naphtha having from 5 to 9 carbon atoms per molecule and methanol. Similarly, U.S. Pat. No. 4,347,118 discloses a method in which pentane is used to extract heavy oil from oil sand. Finally, U.S. Pat. No. 5,143,598 discloses a method that includes adding heptane to oil sand to form an oil-rich heptane phase and then displacing the oil-rich heptane phase with water.

Separating heavy oil from the mineral components of oil sand can be challenging, in part, because oil sand typically includes a wide variety of hydrocarbon components with varying degrees of solubility in particular solvents. For example, oil sand can include large fractions of both straight-chain hydrocarbons and aromatic hydrocarbons. These classes of hydrocarbons respond differently to solvents. Some methods for extracting heavy oil from oil sand include the use of two or more different solvents in serial extraction steps. For example, one solvent can include straight-chain hydrocarbons (e.g., butane through octane), while the other solvent can include aromatic hydrocarbons (e.g., benzene, toluene, and xylene) and/or chlorinated hydrocarbons. Straight-chain hydrocarbons have little or no solvating power for asphaltene and resin fractions contained in oil sand feed stocks.

Biodiesel contains no aromatic rings, but it nevertheless has been surprisingly discovered to be an effective solvent not only for straight chain hydrocarbons, but also for asphaltenes and resins. Thus, biodiesel can be used as a substitute for conventional solvents used to dissolve asphaltene and resin fractions, such as aromatic hydrocarbon and/or chlorinated hydrocarbon solvents. Biodiesel also can be used as a solvent for straight-chain hydrocarbons, so it can function as the sole solvent in a process for the extraction of heavy oil from oil sands and other oil-containing materials.

As mentioned above, biodiesel can be produced from natural fats (e.g., vegetable oils and/or animal fats). In addition to the actual transesterification reaction, converting these natural fats into biodiesel typically involves some refining. Standard refining of natural fats includes: degumming, neutralization, bleaching and deodorizing. Degumming and neutralization remove components (e.g., natural gums and pigments) that may interfere with the transesterification reaction. Bleaching and deodorizing improve the color and smell of the resulting biodiesel, respectively. Bleaching and deodorizing typically are unnecessary if the resulting biodiesel is to be used as a solvent. Thus, to reduce costs, some disclosed embodiments make use of biodiesel derived from natural fats that have not been subjected to bleaching and/or deodorizing steps.

Oil sand extraction processes using biodiesel can have several advantages over conventional oil sand extraction processes. For example, with biodiesel there is less need for expensive safety and vapor containment devices than with conventional solvents. Using biodiesel, oil sand extractions may be performed in open vessels located above ground. Furthermore, biodiesel has been discovered to lower the viscosity of heavy oil more than many other solvents, such as naphtha, gasoil, natural gas distillate and heptane. Low viscosity facilitates separation of heavy oil from the mineral components in oil sand and facilitates pipeline transportation.

A variety of techniques and devices can be used to perform biodiesel extractions. For example, in some embodiments, oil sand ore and biodiesel are mixed in a vessel. The oil-enriched biodiesel phase then is separated from the oil-depleted sand phase, for example, by settling and decanting. The mixing and settling can occur in the same vessel or in separate vessels. Extraction processes using biodiesel can be batch, semi-batch or continuous. Once separated, the oil-enriched biodiesel phase can be used as a fuel or subjected to further processing. For example, the oil-enriched biodiesel phase can be distilled to separate different hydrocarbon fractions. A significant fraction of the biodiesel can be recovered and recycled. In some embodiments, recovered and/or recycled biodiesel is sold in combination with certain heavy oil fractions as a usable product. The oil-depleted sand phase can be returned to the mined-out underground area from which the oil sand ore was extracted.

In an example of a high-capacity operation, directly-mined oil sand is mixed with biodiesel in a pulping drum with a rotating trommel drum having lifter bars. This type of apparatus is adequate to handle large runs of mine ore pieces (such as pieces as large as one foot in diameter). U.S. Pat. No. 4,224,138, which is incorporated herein by reference, discloses this type of system for mixing oil sands with water. The same system, however, also can be used for mixing oil sands with biodiesel. It has been discovered that the dissolution of heavy oil using biodiesel can be faster than with other solvents. Thus, the mixing equipment used for biodiesel extractions can be smaller than it would be for extractions with other solvents. To further increase the rate of dissolution, a crushing step can be included prior to mixing.

Heavy oil extraction using biodiesel can be performed under various processing conditions. For example, it can be performed at room temperature and atmospheric pressure. Higher temperatures, however, may improve the speed and efficiency of the process. Operating temperatures higher than room temperature can be used if, for example, the cost of heating the process is fully offset by the value of a faster rate of dissolution.

In some embodiments of the disclosed method, biodiesel is merely a component of a solvent mixture. Other solvents that can be mixed with biodiesel include, for example, alkanes and oil refinery products, such as gasoil, naphtha, natural gas condensate and petroleum diesel. The percentage of biodiesel in the solvent can be, for example, between about 5% and about 100%, such as between about 20% and about 100% or between about 40% and about 100%. In some embodiments, the ratio of biodiesel to heavy oil to be dissolved is between about 1 and about 10, such as between about 1.5 and about 5 or between about 2 and about 3.

U.S. patent application Ser. No. 11/249,234 (the '234 application), which is incorporated herein by reference, discloses a process for obtaining heavy oil from oil sands. Biodiesel can be used in embodiments of the process disclosed in the '234 application. For example, biodiesel can be a partial or complete substitute for the light aromatic solvent. In addition, an extraction using biodiesel can be substituted for serial extractions using a light aromatic solvent and a volatile hydrocarbon solvent.

U.S. patent application Ser. No. 11/371,327 (the '327 application), which is incorporated herein by reference, discloses a process for recovering asphaltenes from tailings streams. Biodiesel can be used in embodiments of the process disclosed in the '327 application. For example, biodiesel can be used as a component of the hydrophobic agglomeration agent. In addition, solid asphaltene produced in accordance with the '327 application can readily be converted into a liquid product by mixing with small amounts of biodiesel (e.g., 1 liter biodiesel per 1 kg of asphaltene). The resulting material then can be burned in a boiler designed for combustion of heavy fuel oil.

Biodiesel for In-Situ Heavy Oil Recovery

Much of the world's supply of oil sand (e.g., about 90% of the oil sand in the Athabasca region of Canada) is too deep to be mined economically. Furthermore, open pit mining (e.g., at a depth of about 100 meters) often is not economical because the waste-to-ore ratio is too high. In-situ heavy oil recovery, which includes at least some underground mixing and/or processing, can be useful in these situations.

One known method for in-situ recovery of heavy oil from oil sands is steam assisted gravity drainage (SAGD). In this process, steam is used to reduce the viscosity of the heavy oil and to force it to flow into a production well. SAGD has several disadvantages, including high energy consumption. The process typically requires about four barrels of steam per barrel of oil. Moreover, once the oil reaches the surface and cools, it may be too viscous to be transported by pipeline, thus necessitating the use of an expensive diluent.

Another known method for in-situ heavy oil recovery is vapor extraction (VAPEX). This process typically includes the use of light alkane solvents, such as propane and butane, to reduce the viscosity of the heavy oil and to force it to flow into a production well. The alkane solvents, however, have very little ability to dissolve asphaltene and resin fractions, thus resulting in precipitation of these fractions and potential plugging of the formation. The alkane solvents also have high vapor pressures. As a result, significant solvent loses often occur through geologic faults, which often are present in the vicinity of oil deposits.

Biodiesel can be used in an in situ heavy oil recovery process that has many advantages over SAGD and VAPEX. Some embodiments of the disclosed biodiesel process can be referred to as biodiesel assisted gravity drainage (BAGD). Biodiesel can be used to lower the viscosity of heavy oil in underground deposits so that it can be pumped out of the ground. For example, the process may include draining the heavy oil and biodiesel mixture into a mining drift/tunnel located below the oil sand formation and then pumping the mixture above ground. As discussed below, biodiesel has been discovered to be an excellent asphaltene solvent. Heavy oil including asphaltenes is dissolved rapidly in biodiesel, which improves recovery from oil sand formations. The relatively low viscosity of biodiesel/oil mixtures also allows for efficient transportation of these mixtures by pipeline from oil sand formations to production facilities. Moreover, biodiesel makes the process of heavy oil extraction more environmentally benign because it is non-toxic and biodegradable, and safer because it does not produce explosive vapors.

Both SAGD and VAPEX also are generally limited to very deep deposits. If used on shallow deposits, a seal must be positioned over the production zone to prevent any steam or solvent breakouts to the surface and the accompanying discharge of hydrocarbons to the atmosphere. In contrast, since biodiesel has a very low vapor pressure, it requires no overburden to be contained. Thus, BAGD may be a more economical method for extracting oil from the many deposits that are too deep for open pit mining and too shallow for SAGD or VAPEX.

In some BAGD embodiments, central drifts or tunnels are placed above, below and/or to the side of an oil sand ore zone. From these drifts or tunnels, biodiesel solvent can be injected to solubilize hydrocarbons in the oil sand and/or received after injection. For example, biodiesel solvent can be injected into an oil sand formation through a hole in a drift or tunnel above, below or along the side the formation and drained through the same hole or a different hole in the same or a different drift or tunnel. Alternatively, biodiesel solvent can be injected from the surface above an oil sand formation and then gravity drained through the formation and into a drift or tunnel below the formation (e.g., between about 10 and about 100 feet below the formation). The biodiesel and heavy oil mixture then can be recovered from the drift or tunnel. Due to the low vapor pressure and low toxicity of biodiesel, mining operators can readily enter the drifts or tunnels for operation of fluid injection and receiving controls. Underground or above ground heap or vat leaching analogous to that used in the gold, cooper and nickel industries is yet another potential implementation.

FIG. 1 illustrates one example of a BAGD process. Biodiesel 10 first is purchased and stored in a vessel 12. The vessel 12 can be constructed of any compatible material, such as stainless steel. From the vessel 12, a process biodiesel stream 14 is injected into an oil sand formation 16. This injection can occur, for example, from the surface through injection holes or from mining drifts or tunnels located above, below and/or to the side of the oil sand formation 16. Within the oil sand formation 16, the biodiesel dissolves heavy oil to form a mixture 18 of biodiesel, heavy oil and minor amounts of water. The mixture 18 typically has a relatively low viscosity, so it can be transported efficiently to the surface for further processing. As shown in FIG. 1, the mixture 18 is pumped out of the oil sand formation 16 and into a separator 20. For example, the mixture 18 can be collected in a drift or tunnel and then pumped to the separator 20 through a pipeline.

Within the separator 20, the mixture 18 is separated into diluted heavy oil 22, a gas phase 24 and a stream 26 including water and residual oil. This separation can occur, for example, by vacuum stripping. The gas phase 24 typically includes methane, ethane, and propane and can be sent to a gas recovery plant. The stream 26 is sent to another separator 28 for separation into residual oil 30 and water 32. This separation can occur, for example, by gravity separation. After exiting the separator 28, the water 32 is sent to disposal. The residual oil 30 exiting the separator 28 and the diluted heavy oil 22 exiting the separator 20 are routed to a vessel 34 for storage. A diluted heavy oil product 36 then can be removed from the vessel 34 as needed for use or sale. The diluted heavy oil product 36 also can be subjected to a further separation step (e.g., heating and stripping) whereby some of the biodiesel solvent is recovered and recycled to vessel 12.

Microbial Processes for Making Biodiesel

Biodiesel currently is produced by transesterification of tri-glyceride oils. Biodiesel also can be made, however, by alcoholysis of fatty acids (i.e., organic or carboxylic acids). U.S. Pat. Nos. 6,768,015, 6,965,044 and 6,822,105, which are incorporated by reference, disclose the conversion of "free" fatty acids into alkyl esters by transesterification with alcohol. Potential fatty acid feed stocks for the production of biodiesel include bioliquified asphaltenes, such as bioliquified petroleum asphaltenes and bioliquified coal. For example, *pennicilium* cultures are able to metabolize on carboniferous materials and excrete fatty acids, such as tricarboxilic acids. Such tricarboxilic acids can react with methanol in a transesterification reaction to produce esters. Thus, cooking bioliquified asphaltenes with an alcohol produces biodiesel. Treatment of asphaltenes with similar fungi produces organic acids, which also can be converted into biodiesel by reaction with alcohol. In some cases, the carbon chain lengths of the esters produced by microbial processes are not within the biodiesel range, but can be modified by catalysis and/or hydrogenation to form biodiesel.

Some processes are known for partially breaking down asphaltenes. For example, ruthenium-ion-catalyzed oxidation (RICO) involves selectively oxidizing aromatic substructures to yield aliphatic carbonic acids and diacids. Additional processes are disclosed in U.S. patent application Ser. No. 11/450,591, which is incorporated herein by reference. The hydrocarbon products from processing of coal by RICO and other processes can be converted into fatty acids using an additional biological step.

Asphaltenes are found in both petroleum products and coal. Coal asphaltenes typically have less complex structures than petroleum asphaltenes. As a result, coal asphaltenes typically are more easily digested by microbial processes. Some conventional processes exist for the solubilization of low rank coals using various fungi. One such process is disclosed, for example, in U.S. Pat. No. 4,846,964, which is incorporated herein by reference. Known processes, however, do not disclose conversion of the resulting fatty acids into biodiesel.

Figure 2:
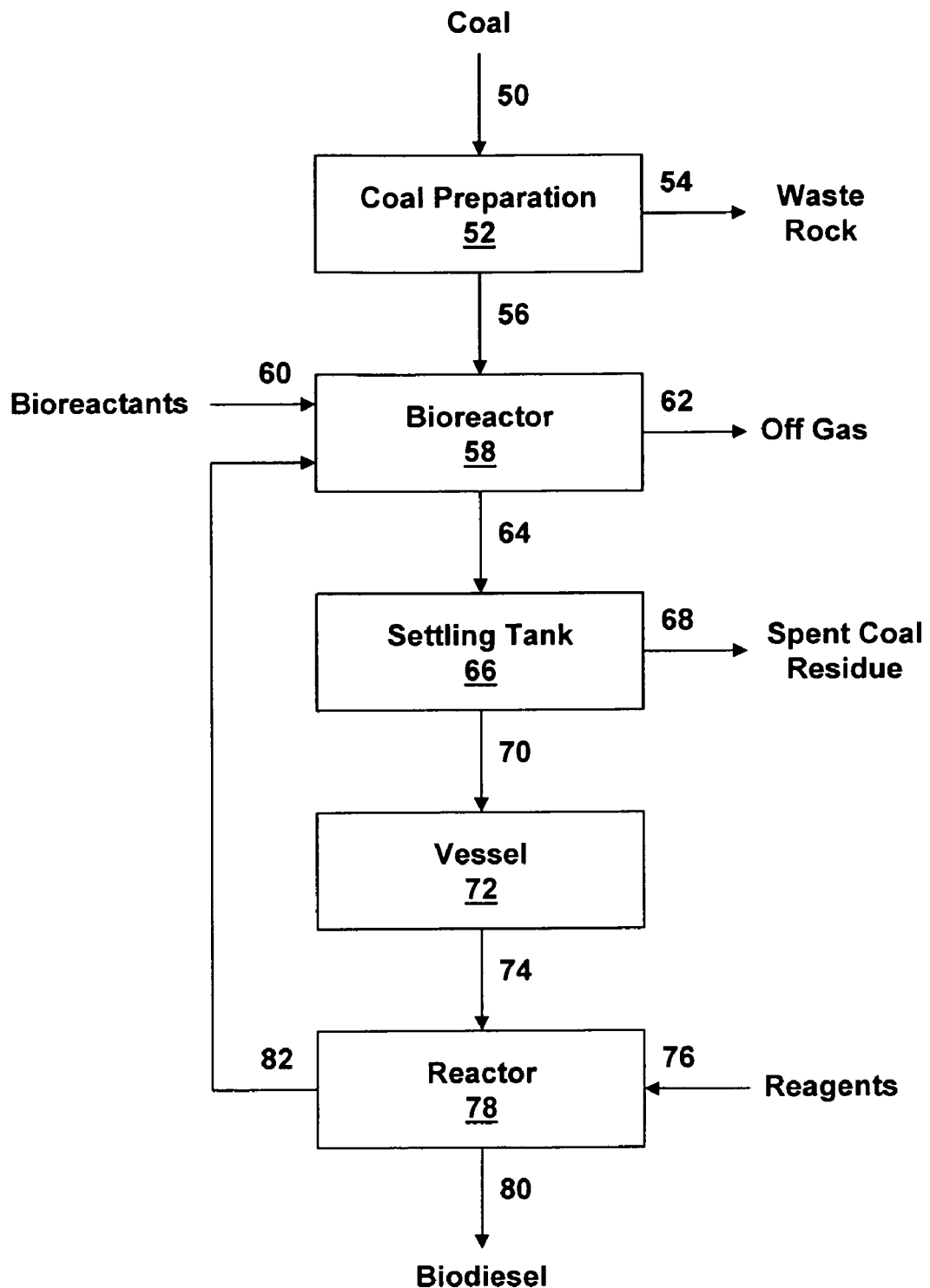
FIG. 2 is a schematic diagram representing embodiments of a process and apparatus for converting coal into biodiesel.

FIG. 2 shows one example of a process for converting coal into biodiesel. Coal 50 first is mined and sent to a coal preparation area 52. The coal preparation step can include, for example, removal of waste rock 54. Prepared coal 56 then is routed to a bioreactor 58. Bioreactors compatible with this process are commercially available. Within the bioreactor 58, the prepared coal 56 is mixed with bioreactants 60. One or more microorganism is present in the bioreactor 58 or introduced with the bioreactants 60. Useful microorganisms include fungi, such as: *acremonium, aspergillus, candida, coriolus versicolor, cunninghamella, ganoderma applanatum, heterobasidion annosum, mucor, paecilomyces, penicillium, perenniporia subacida, perenniporia tephrosia, phanerochaete chrysosporium, pleurotus ostreatus, poria monticola, polyporus dryophilus, pycnoporus cinnabarinus, rigidoporus ulmarius, sporothrix* and *xylaria hypoxylon*. The bioreactants 60 also can include one or more surfactant, inhibitor, and/or solvent. The temperature and pressure inside the bioreactor can be selected to promote digestion of the asphaltenes. In some embodiments, the temperature is about room temperature and the pressure is about 1 atm. The bioreaction process can be batch, semi-batch or continuous. The process is allowed to continue until a certain percentage of the asphaltenes have been digested, such as between about 5% and about 100% or between about 40% and about 90%. The residence time of material within the bioreactor can be, for example, between about 2 hours and about 168 hours or between about 8 hours and about 72 hours. Off gas 62 exits the bioreactor 58 during processing.

After processing, a bioreactor product 64 is moved into a settling tank 66. Within the settling tank 66, spent coal residue 68 is settled from the bioreactor product 64 and removed. The spent coal residue 68 can be sent to waste or processed again to recover additional hydrocarbons. Further processing of the spent coal residue 68 can include grinding it into coarse particles. A resulting bioliquor 70 exiting the settling tank 66 is routed into a vessel 72 to be stored prior to conversion into biodiesel.

Upon demand, a bioliquor stream 74 is removed from the vessel 72 and mixed with reagents 76 in a reactor 78 to produce biodiesel 80. The reagents 76 typically include an alcohol (e.g., methanol) and a catalyst (e.g., an enzyme). Formation of biodiesel may occur by one or both of the following reactions:

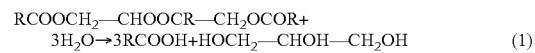

$$RCOOCH_2\text{---}CHOOCR\text{---}CH_2OCOR + 3H_2O \rightarrow 3RCOOH + HOCH_2\text{---}CHOH\text{---}CH_2OH \qquad (1)$$

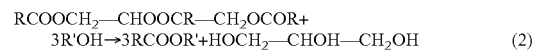

$$RCOOCH_2\text{---}CHOOCR\text{---}CH_2OCOR + 3R'OH \rightarrow 3RCOOR' + HOCH_2\text{---}CHOH\text{---}CH_2OH \qquad (2)$$

The reaction can be carried out, for example, at a temperature between about 10° C. and about 75° C., such as between about 15° C. and about 45° C. It can be batch, semi-batch or continuous. After the reaction, the biodiesel 80 is sent to be used or sold and residual bioliquor 82 is recycled back to the bioreactor 58 to repeat the process. Coal conversion using this process may be greater than about 50%, such as between about 60% and about 70%.

EXAMPLES

The following examples are provided to illustrate certain particular embodiments of the disclosure. Additional embodiments not limited to the particular features described are consistent with the following examples.

The tests described in these examples were performed using biodiesel obtained from Bently Biofuels (Minden, Nev.).

Example 1

Heavy Oil Extraction from Solid Pitch

In an initial trial, biodiesel was tested on pitch derived from a process to convert heavy oil into light oil by steam cracking. The pitch was a fluid at 150° C., but rock hard at ambient temperature. It was found that about 500 grams of the rock hard pitch could be readily dissolved in about 1 liter of biodiesel at room temperature. In an additional trial, about 40 grams of the pitch (broken into pieces having effective diameters smaller than about 10 mm) was mixed with about 80 grams of biodiesel in an agitation vessel. Solid lumps were still present after one hour of agitation. All lumps disappeared and all of the pitch pieces were dissolved in the biodiesel after two-hours of agitation. The resulting solution was highly viscous.

Example 2

Heavy Oil Extraction from Oil Sand

In further testing, several oil sand samples were exposed to biodiesel under different conditions. The level of extraction was determined based on color changes in the biodiesel and observation of the remaining solids after testing. Two different extraction vessels were used. One vessel was designed for vigorous mixing and the other vessel was designed for gentle mixing. In the vigorous mixing trials, solid samples and biodiesel were placed in a 2-liter stainless steel vessel. The contents of the vessel then were agitated with a mixer having a three-blade impeller for a predetermined time. The mixer had a variable speed controller with settings from zero to ten, allowing the degree of agitation to be adjusted. It is estimated that an agitator setting of ten represents at least 500 rpm. All tests were performed at level two. In the gentle mixing trials, solid samples and biodiesel were placed in a 2-liter polypropylene bottle with a wide opening. The bottle then was placed on a pair of rollers having an adjustable rotating speed. The bottle rotating speed was adjusted to between 27 and 30 rpm during the testing. The bottle included no lifters, so the solid samples remained on the bottom during the rolling.

In these trials, biodiesel was tested as a replacement for toluene for solubilizing residual asphaltenes. Gentle mixing, as described above, was performed on an oil sand sample with over 80% of the heavy oil already removed by previous extraction with heptane. About 20% of the heavy oil phase remained insoluble in the heptane and therefore was classified as asphaltene. In this trial, 100 grams of the heptane treated oil sand was mixed with 100 grams of biodiesel, giving a mixture with a 50% solids density. Despite the low concentration of asphaltene and residual heavy oil in the sample, the color of the biodiesel changed to dark brown rapidly indicating rapid extraction of the asphaltene and residual heavy oil from the oil sand. After one hour of agitation, the resulting mixture was filtered to separate the sand from the biodiesel and heavy oil liquid. This filtration was slow due to the viscosity of the liquid. Once separated, the sands were found to be light brown. This indicated that most or all of the asphaltene and residual heavy oil was dissolved into the biodiesel.

A trial with vigorous mixing, as described above, was performed on an unprocessed oil sand sample. This material was particularly dry and had aged over time. In this trial, 200 grams of oil sand was mixed with 72 grams of biodiesel. The ratio of solvent to heavy oil was about three-to-one. Due to the small amount of biodiesel, the intensity of agitation had to be reduced. After two hours of agitation, a few lumps remained, but most lumps were quite unexpectedly dissolved.

Example 3

Varying the Biodiesel to Heavy Oil Ratio

Two tests were carried out with different ratios of biodiesel to heavy oil. The heavy oil content in the tested samples was assumed to be about 15%. In a first trial, the tested ratio was ten parts biodiesel to one part heavy oil (350 mL biodiesel and 200 grams oil sand). In a second trial, the tested ratio was five parts biodiesel to one part heavy oil (175 mL biodiesel and 200 grams oil sand). The mixtures were rolled in bottles overnight, as described in Example 1. After this process, all of the lumps were dissolved. The mixtures included liquid and individual grains of sand. This indicated near complete heavy oil extraction in both trials. Normal filtering was difficult due to the presence of fine clay particles, but gravity settling was quite fast. Vacuum filtering was used to separate the sand from the biodiesel and heavy oil mixture in the five-to-one trial. Once separated, the viscosity of the dilute heavy oil solutions was measured with a rotating disk viscometer. The viscosity of the ten-to-one dilute heavy oil was 6 cp (average of three measurements). The viscosity of the five-to-one dilute heavy oil was 14 cp (average of three measurements). These values can be compared to a viscosity of about 5 cp for fresh biodiesel and 1 cp for water at 20° C. Many oil products have higher viscosities, such as gas oil with a viscosity of about 50 cp.

The separated solids from both trials were vigorously mixed with water to determine whether water would replace the biodiesel residue. Due to the high hydrophobicity of the solids, no mixing with water took place. This result confirmed that potential issues related to the formation water-oil emulsions are not to be expected when biodiesel is used in oil sands extractions. If water forms a stable emulsion with the oil phase, as can occur when naphtha is used in oil sands extractions, it can be difficult to separate and can ruin the product.

Example 4

Mixing Biodiesel with Asphaltene Flotation Concentrate

Asphaltene flotation concentrate containing about 40% moisture was mixed with biodiesel. In a first trial, 200 grams of asphaltene flotation concentrate was mixed with 60 grams of biodiesel. This gave a ratio of two parts asphaltene (without moisture) to one part biodiesel. At this ratio, all of the biodiesel was absorbed into the concentrate without mixing. Next, 40 additional grams of biodiesel was added and medium to strong agitation was applied for two hours. The asphaltene flotation concentrate was well mixed with biodiesel and resembled a sticky paste (i.e., more liquid than powder). No indication of the presence of water was observed. Another 34 grams of biodiesel then was added to the paste to determine if the water would separate. After 10 minutes of strong agitation, this additional biodiesel was again well mixed. No sign of water separation was observed.

Example 6

Bioliquefication of Coal

Figure 3:
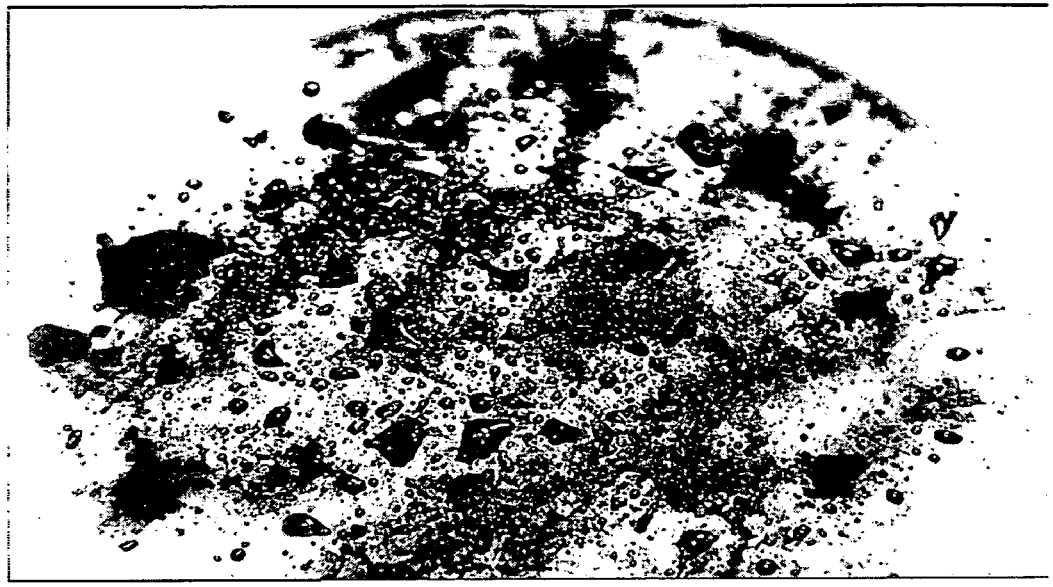
FIG. 3 is a photograph of solid coal being liquefied on a Petri dish by *pennicilum waxmanii*.
Figure 4:
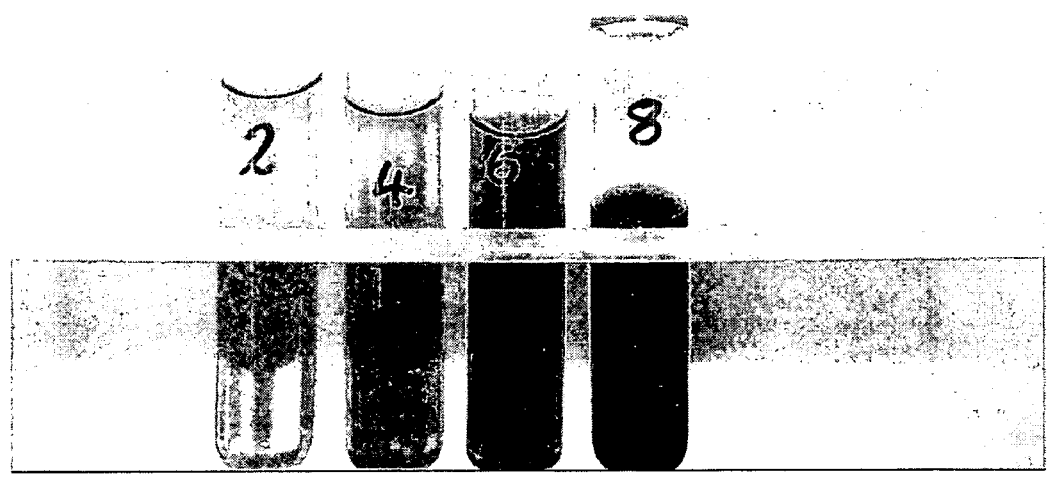
FIG. 4 is a photograph of beakers of coal solutions after 2, 4, 6 and 8 days of bioleaching with *pennicilum waxmanii*.
Figure 5:
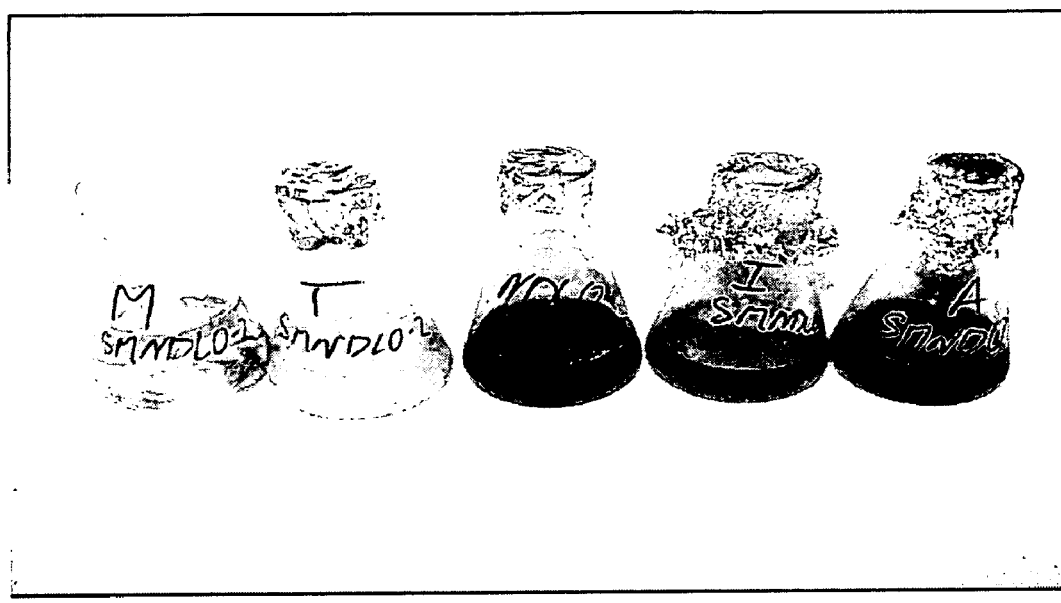
FIG. 5 is a photograph of flasks containing coal solutions with different levels of asphaltene dissolution after exposure to different cultures of *pennicilum*.

This example describes the results of several laboratory experiments on the conversion of low rank coal into black liquid using fungi. FIG. 3 shows the liquefaction of coal using *penicillium waxmanii* cultures. Within days, the solid coal phase on the Petri dish began to be liquefied. FIG. 4 demonstrates the liquefaction kinetics of *penicillium waxmanii* by showing the changing color of samples after 2, 4, 6 and 8 days of bioleaching. Dissolution of asphaltenes in the coal over time caused the samples to become darker. FIG. 5 shows flasks containing coal and different cultures of *penicillium*. The different shades of the liquid suggest that the some cultures were more effective at digesting the coal than others.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method for obtaining heavy oil, comprising:
   mixing a material comprising heavy oil and sand with a solvent comprising biodiesel to form a mixture; and
   separating the mixture into a oil-enriched solvent phase and a residual sand phase;

wherein the mixing and separating are carried out at atmospheric pressure.

2. The method according to claim 1, wherein the material comprising heavy oil and sand is oil sand.

3. The method according to claim 1, wherein the material comprising heavy oil and sand is a petroleum-containing substrate.

4. The method according to claim 1, wherein the solvent comprises between about 5% and about 100% biodiesel.

5. The method according to claim 1, further comprising transporting the residual sand phase underground to a location from which the material comprising heavy oil and sand was withdrawn.

6. The method according to claim 1, wherein the biodiesel is derived from natural fats that have not been subjected to bleaching and/or deodorizing.

* * * * *